United States Patent
Layfield et al.

(10) Patent No.: US 6,773,673 B1
(45) Date of Patent: Aug. 10, 2004

(54) RADIATION HANDLING SYSTEM AND SET

(75) Inventors: Dominick Layfield, Somerville, MA (US); José Venegas, Swampscott, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/674,137

(22) PCT Filed: Apr. 26, 1999

(86) PCT No.: PCT/US99/08981

§ 371 (c)(1),
(2), (4) Date: Dec. 4, 2000

(87) PCT Pub. No.: WO99/56117

PCT Pub. Date: Nov. 4, 1999

Related U.S. Application Data

(60) Provisional application No. 60/083,133, filed on Apr. 27, 1998.

(51) Int. Cl.[7] .......................... G01N 24/00; G01N 37/00
(52) U.S. Cl. ......................................... 422/81; 422/100
(58) Field of Search ..................... 422/81, 100; 436/57, 436/174

(56) References Cited

U.S. PATENT DOCUMENTS 5,168,901 A    12/1992  Marks ......................... 137/884
5,223,434 A    6/1993   Kanno et al. .................. 436/56
5,326,532 A    7/1994   Taylor
5,468,355 A    11/1995  Shefer et al. ............. 204/157.2
5,482,865 A    1/1996   Ferrieri et al. ................. 436/56
5,514,071 A    5/1996   Sielaff, Jr. et al. .............. 600/3

FOREIGN PATENT DOCUMENTS

JP          05249244 B1    9/1993

OTHER PUBLICATIONS

J. C. Clark et al., "Short-lived Radioactive Gases for Clinical Use" (*Butterworths London and Boston*) (1975) Chapter 6 (Nitrogen-13) *Exerps*.

*Primary Examiner*—Jeffrey R. Snay
(74) *Attorney, Agent, or Firm*—Nutter McClennen & Fish LLP

(57) ABSTRACT

A radioactive material such as an unstable isotopic gas is provided to a receiving chamber (1) directly from a source to form a purified or enriched bubble. The bubble is passed to a fluid handling set for preparation of the reagent or other delivery system. In an exemplary embodiment trace amounts of nitrogen-13 are concentrated in a receiving chamber and passed into a small bubble of carrier gas. The carrier gas is then delivered into a fluid handling set. The fluid handling set connects to a pressure syringe (50) and a passive syringe (60), and further includes a plurality of flushable valves (22–27) interconnected as a closed unit by tubing (21) to form a switchable or finite state flow network in which the pressure syringe may back flush the tubing, mix the isotope in a delivery liquid, and transfer the mixed liquid to an output for diagnostic imaging or other use.

14 Claims, 8 Drawing Sheets

RADIATION HANDLING SYSTEM AND SET

CROSS-REFERENCE TO RELATED APPLICATIONS

This application claims the benefit of provisional application Ser. No. 60/083,133, filed Apr. 27, 1998.

STATEMENT REGARDING FEDERALLY SPONSORED RESEARCH

Not Applicable.

BACKGROUND OF THE INVENTION

The present invention relates to the preparation and use of radioactive isotopes for biological purposes such as labeling, marking, imaging and diagnostics. Such applications generally utilize a single element containing minor amounts of an unstable isotope, which must be generally formed into a simple compound that is incorporated into a solution or reagent which undergoes a known or predictable interaction with the biological system being studied. Thus, for example, radionuclides are often added as labels to a substance that binds to a nucleic acid to indicate the presence of a particular substrate, termination or functional group. Similarly, materials which are taken up by particular biological systems may be labeled for treatment or imaging purposes. Aerosols or radio-labeled fluids may also be used for blood flow or lung function diagnostic imaging studies.

In general, it is necessary that radioactive materials be handled in such a way as to not expose the operator to radiation. Thus they are preferably handled under robotic control or automated conditions. It is desirable that the radioisotopes involved have a short half life, so as to automatically limit the exposure of the subject to radiation, and to facilitate proper disposal. However, materials with a short half life cannot be compounded in advance or stored for lengthy times. Such radionuclides must therefore be manufactured at or near to the site of intended use. In these cases the purification and preparation of the radionuclide in a suitable delivery system must also be accomplished locally. The brevity of the nuclide half life may further complicate its handling and processing. These factors have sometimes prevented the acceptance or use of otherwise worthwhile radionuclide-based procedures.

It would therefore be desirable to provide a convenient system for preparing radionuclides for biological use.

It would also be desirable to provide such a system for handling a radionuclide in an automated fashion without exposing the operator to radiation.

It would further be desirable to provide such a system useful for short-lived materials or small batches to enable the routine use of such materials in individual procedures.

SUMMARY OF THE INVENTION

These and other desirable features are achieved in a system in accordance with the present invention by providing a radioactive marker material such as an unstable isotopic gas to a receiving chamber directly from a source to undergo initial cleansing or concentration, and passing the material into a fluid handling set for automated preparation of the reagent or actual delivery system. In an exemplary embodiment, trace amounts of $^{13}N$, created by proton bombardment of a target at a cyclotron, pass to a receiving chamber, are cleansed and pass into a small bubble of carrier gas. The carrier gas is then delivered into a fluid handling set. The fluid handling set includes or connects to a pressure syringe and a passive syringe, and further includes a plurality, of flushable valves interconnected by tubing in a closed unit to form a flow network in which the pressure syringe may back-flush the tubing, mix the isotope in a delivery liquid, and transfer the mixed liquid to an output for diagnostic imaging or other use. The fluid handling set, which is a closed and preferably sterile unit, may include the receiving chamber 1, and it mounts in a fixed console of operating motors and condition sensors to control the various steps of fluid handling and delivery, and to effect safety functions which enable the system to connect directly to a catheter or to a vascular injection system for use on human beings.

In a preferred embodiment, the receiving chamber 1 is substantially rigid, but has a region of limited or unidirectional compliance. The chamber receives a flow of trace isotope in a bulk gas, operating to remove the bulk gas while the radionuclide accumulates in a bubble at the outlet port of the chamber. Compliance of the receiving chamber may be effected by means of an elastic wall tensioned against a rigid support such that the wall flexes outwardly under pressure to accommodate the inflow of carrier gas but may not bow inwardly. This maintains the chamber volume above a fixed minimum, and prevents liquid from leaving the chamber when suction is applied at the top. In an illustrative system, nitrogen-13 is generated by cyclotron bombardment of a target with accelerated particles, and when the target has attained a sufficient level of radioactivity, the sample is passed to the receiving chamber and the $CO_2$ with trace $^{13}NN$ is bubbled into a sodium hydroxide solution. The one-way compliant wall allows a large flow to be received and maintained under pressure to accommodate the different rates of carrier delivery and carrier removal effected at this stage. The $CO_2$ reacts with and is effectively taken up by the sodium hydroxide solution, while the desired nuclide concentrates at a gas-filled plenum at the top of the receiving chamber, where it is accessed at the outlet port using a closed sterile set to effect transfer, mixing and delivery in a form useful for medical imaging. The fluid handling set includes a plurality of three way valves or medical infusion stopcocks that are preconnected together via small bore tubing to form a flow path. Two of the stopcocks each have a third port, which are attached to syringe bodies. One operates as an active bidirectional pump, while various motors and sensors in the console operate and control the position of the stopcock handles to achieve transfer, mixing and delivery of the radionuclide.

BRIEF DESCRIPTION OF THE DRAWINGS

The invention will be more fully understood from the following detailed description taken in conjunction with the accompanying drawings, in which.

DETAILED DESCRIPTION OF THE DRAWINGS

Figure 1:
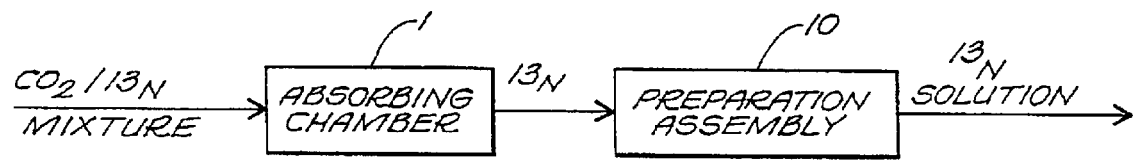
FIG. 1 is a flow chart illustrating major steps of the preparation process of the present system.

In accordance with a principal aspect of the present invention, there is provided a system for automated and isolated handling of a hazardous material, such as a radionuclide, for biological or medical use. The system includes a sterile set defining the path of the nuclide from a source or process chamber to its end use which, in the illustrated embodiment, involves injection into a patient. Other potential end uses may include specialized labeling, microanalytic or synthesis applications. As shown in FIG. 1 for a representative system, the radionuclide, which in this case is nitrogen-13, passes from a source to a conditioning or purification chamber 1 which produces a small mass or bubble of the concentrated radionuclide for delivery to the preparation portion 10 of the system. The preparation portion 10 dissolves the nuclide in a saline solution for injection in a patient, and may directly inject the prepared solution into the patient.

By way of technical background for this embodiment, the use of nitrogen-13 in gaseous form for medical imaging procedures was pioneered at the Hammersmith Hospital, in London, several decades ago. The radionuclide is produced by bombardment in a cyclotron using a number of possible target systems and sweep gases. Further details may be found in the text Short-lived Radioactive Gases for Clinical Use of J. C. Clark and P. D. Buckingham (Butterworth, London and Boston) pp 190–200. That text is hereby incorporated herein by reference. Nitrogen-13 is only very slightly soluble in blood, and when injected in solution in the blood stream, quickly leaves the blood and accumulates at the blood-air exchange interface in the lung. Its decay creates positrons which may provide excellent three dimensional PET images of the lung, for evaluation of both perfusion and ventilation. However, the difficulties of using this radionuclide have effectively prevented its adoption in hospital settings. Much of the discussion below is applicable to other gaseous radionuclides such as oxygen-15, or radionuclides incorporated in a gaseous medium, or in a liquid with appropriate modifications. However, the preparation and use of nitrogen-13 presents a number of technical difficulties and will therefore be discussed more fully to illustrate aspects of a system and components of the present invention.

Figure 1A:
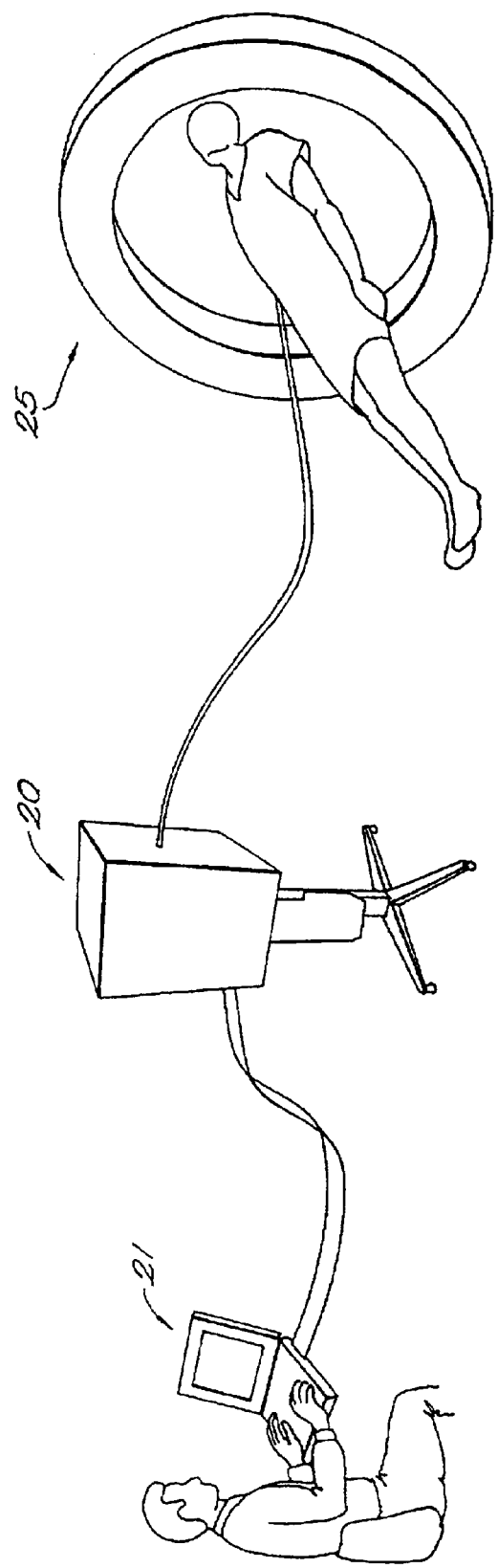
FIG. 1A illustrates the system showing representative components in use for positron emission tomography.

In accordance with a principal aspect of the present invention the source radionuclide is provided in a relatively crude or bulk form, for example in a sweep gas or target fluid from a cyclotron, or in other primitive or intermediate form, and flows through the system to directly enter the patient or be applied to some other sterile or purified application such as marking, analysis or synthesis of a pure product. As shown in FIG. 1A it is generally contemplated that the system 20 will be a small cabinet, desktop or other stand-alone unit containing the sub-assemblies 1, 10 (FIG. 1), and which attaches to the source and to tie patient either directly or via a small intermediate assembly. For example, the unit 20 may connect to the source through a filtration unit or the like, and to the patient via an infusion line, port or pressurized timed injector or the like. However, most preferably the connection to the source and to the patient are as direct as possible so that little dead space, wasted volume, delay time or regions of radiation exposure are interposed between the source and the patient.

As further shown in FIG. 1A, the invention generally contemplates that the unit 20 will be controlled as to several parameters discussed below by a connection to a keyboard/processor assembly 21. Also the specific nitrogen-13 embodiment is used in conjunction with an imaging or detection assembly 25. The assembly 25 of FIG. 1A is a detector array which encircles the patient and is configured for positron emission tomography, to simultaneously detect the pair of annihilation photons emitted in opposite directions by positron-electron annihilations as the radionuclide decays. The detector 25 provides its detection signals to a processor for construction of a three dimensional image of the distribution of the positron-emitting radionuclide. Other suitable detectors include single-sided detector arrays, or even photographic plate cameras which register and record the received annihilation photons on a plate of film. However, a positron emission tomography (PET) instrument is the preferred detection instrument for the illustrated process.

Figure 2:
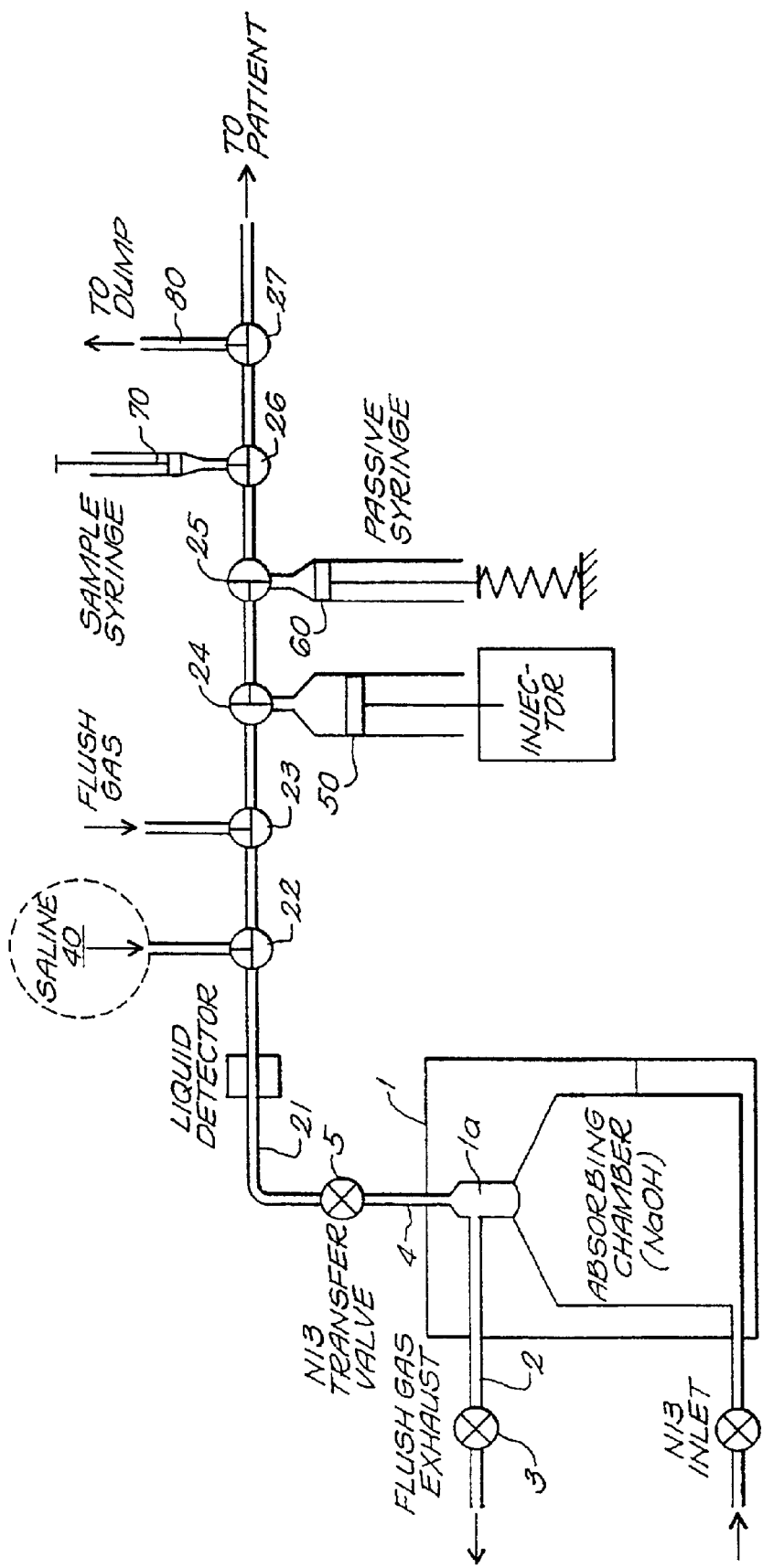
FIG. 2 illustrates system architecture as applied to a nitrogen 13 radionuclide.

FIG. 2 illustrates functional component of the units 1, 10 of FIG. 1. As shown, the unit 1 for carrying out preliminary cleansing or refinement of the radionuclide in this case includes an absorbing chamber through which the nitrogen-13 bubbles to remove the $CO_2$ sweep or residual target gas as the material arrives from the cyclotron source. The absorbing chamber 1 is filled with sodium hydroxide solution and is shaped with an inverted funnel cap that channels unabsorbed gas upward to a plenum 1a at the top of the chamber. Plenum 1a connects on the one hand to an exhaust port 2 controlled by an exhaust valve 3 and, on the other hand, to an outlet port 4 controlled by transfer valve 5. The outlet port connects to the main process line 21 of the sub-assembly 10, which as noted above resides within the preparation console 20 (FIG. 1A) forming an inlet thereof and extending therethrough to the patient or end use. As described further below, chamber 1 may also be located within the console 20.

As further shown in FIG. 2, the functional flow control and handling units appearing in the preparation console 20 include in addition to the flow line 21 a plurality of sterile three-way valves or stopcocks 22, . . . 27 each of which has two of its three ports connected to the line 21, and its third port connected to an inlet, outlet or syringe. The distal end of line 21 forms the output path from console 20. Each of the stopcocks 22–27 may be identical, and advantageously the stopcocks together with tube 21 are connected together and initially provided as a closed and sterile unit packaged in a manner similar, for example, to a medical infusion set. Each stopcock thus has one "free" port which is connected to allow material to enter, leave, or be moved along line 21. These third ports are attached to a source of sterile saline fluid 40, an active injector syringe 50, a source of flush fluid, and a passive holding syringe 60. In addition, a sample syringe 70 connects at stopcock 26, and an outlet line 80 to a dump, or waste vessel, extends from stopcock 27. These elements may also be connected as part of the set, although, as will be understood from the discussion below, variations are possible. The function of the sample syringe may be implemented instead by providing a small plenum with a pierceable septum connected to the third port of stopcock 26, and the line 80 may simply terminate with a spike port for attaching to a suitable collection vessel or transfer mechanism.

As further illustrated in FIG. 2, the passive syringe is spring loaded so that it is normally biased to a non-extended, closed or minimal volume configuration. Thus, when a pressurized flow appears along line 21 and is directed into the syringe 60 by stopcock 25, its piston moves outwardly to form an adaptive chamber that changes volume under pressure for receiving the fluid in the line 21.

In accordance with a principal aspect of the present invention, the sterile set 21 includes a set of connected stopcocks and a syringe 50 all configured to fit within the control console (described further below) and to be manipulated by servomotor elements therein to carry out the radionuclide preparation and delivery to the patient. In a representative preparation and delivery protocol, the stopcocks are set to positions such that one or more stopcocks block the inlet, outlet or intermediate portion of the set, while one or more stopcocks are open to interconnect various portions of the path for receiving, preparing or delivering the radionuclide. In particular, the set 21 defines a finite state flow path formed of sterile single use disposable elements that fit within a console adapted to secure and control both sets of elements. Advantageously, the console 20 may be configured as a cabinet having separate compartments and which may, for example, be hinged to open for inserting and changing the set. In the prototype, the receiving chamber 1 is housed in the back half with its outlet line 4 (FIG. 1A) connecting through the middle wall of the cabinet so that the fluid line 21 (FIG. 2), runs through an array of stopcock or syringe receiving recesses and control elements laid out along a path in the front half of the cabinet.

In this embodiment, the apparatus is conveniently divided into those parts that do not contact the sterile solution, and those parts which do. The parts which contact the saline directly are sterile, and are assembled from disposable medical components. These include all of the tubing downstream of the liquid detector, the stopcocks, and the three syringes 50, 60, 70 which are disposable, and are to be replaced for each patient. These components are mounted on the front panel of the main unit, so that they can be changed quickly. The remaining parts of the system do not contact the saline, and may advantageously be made of reusable components. Thus the absorbing chamber 1, and the various solenoid valves and tubing that connect to it may be permanently installed. Preferably, the system is enclosed in a cabinet which is connected to a high flow-rate vacuum to maintain a steady flow into the cabinet through its small openings, so that any leaks of radioactivity within the system are contained and the radioactive material is removed.

The cabinet is divided into three compartments. The rear compartment, accessible via a rear door, contains the absorbing chamber and a dump tank. This compartment is watertight so that a catastrophic failure of the absorbing chamber will not result in escape of sodium hydroxide. A central compartment houses all of the electronics of the apparatus, and is protected from contact with any liquid that may leak from a failing component or connection. The front of the cabinet forms a door which encloses the front panel, allowing easy access to components of the system that need to be changed frequently. Preferably the syringes mount on this panel.

Figure 3:
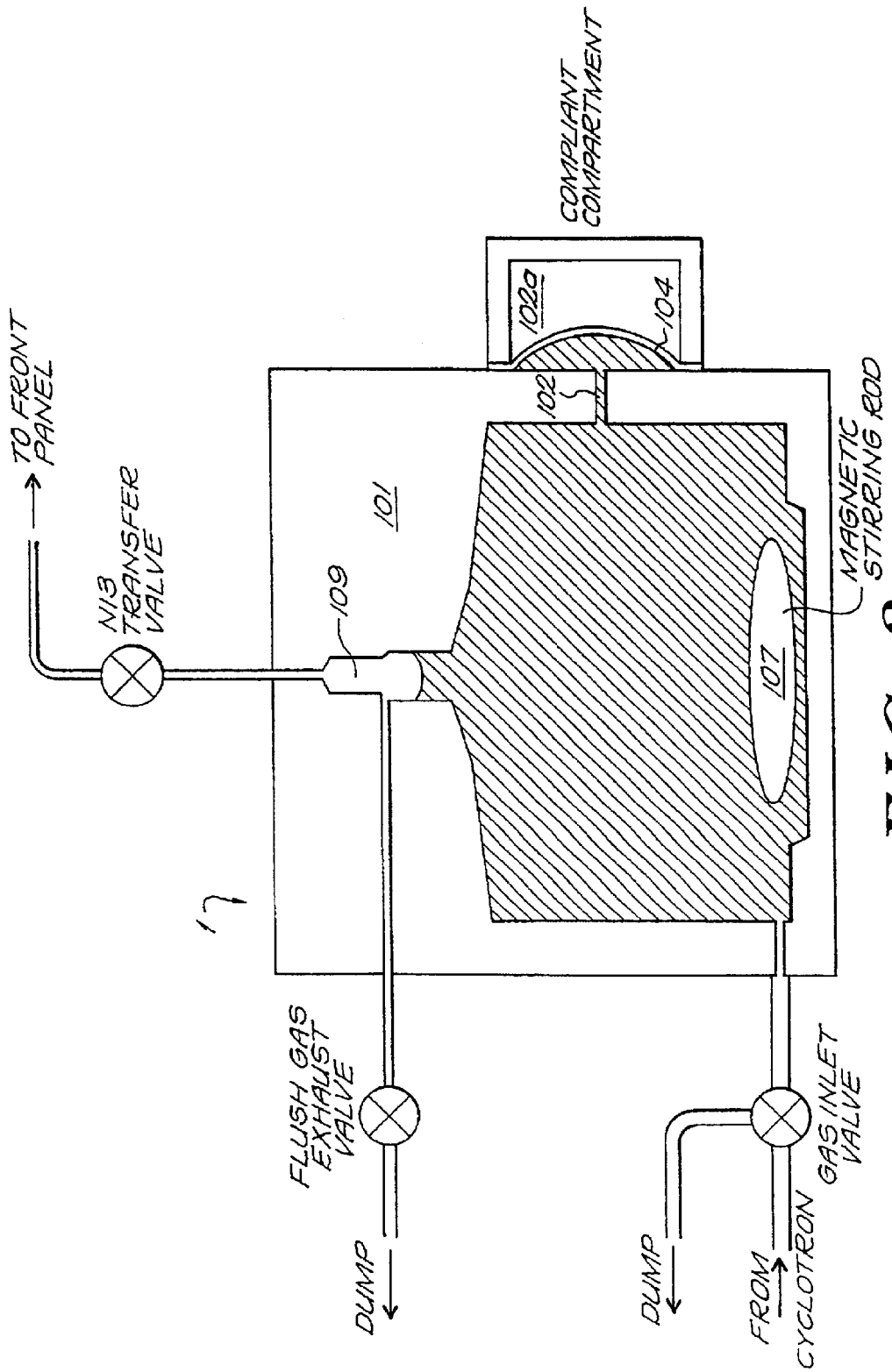
FIG. 3 illustrates a preferred construction of a receiving chamber for the system of FIG. 2.

FIG. 3 shows a preferred construction for the receiving chamber 1, which may be formed of a strong medical grade polymer. As shown, the receiving vessel 1 is configured with a rigid housing 101 which may for example be formed of a hard plastic and having an interior with a major lower portion configured with a sloped roof leading to a chimney-like upper portion or outlet plenum 109 of defined volume. The vessel 101 is configured to fit on a magnetic base such as a stand having an internally mounted rotating permanent magnet driver mechanism positioned below the chamber support surface, and a magnetic stirring rod 107 is positioned in the bottom of the vessel 1. The main chamber communicates through a passage 102 to a secondary chamber 101a bounded by a flexible elastic membrane or wall 104 positioned over the passage 102. This serves as a compliant chamber; the membrane 104 bends outwardly as pressure increases in the chamber 1 and fluid flows through the passage into the secondary chamber. However, housing 101 is rigid and the passage 102 is relatively small, or else may consist of a number of small passages such that the wall below the flexible sheet 104 forms a perforated plate that supports the sheet and effectively prevents the sheet 104 from moving inwardly in response to negative pressure. This arrangement provides a stable volume within chamber 1, and accommodates a large influx of fluid so that when radioactive material from the cyclotron enters the inlet, a large bolus of material may be received, increasing the pressure and allowing the material to more effectively react in the absorbing chamber at the slower process rate of absorption therein. As discussed briefly above for the illustrated $CO_2$/nitrogen-13 material, chamber 1 is filled with a sodium hydroxide solution and is gently stirred by a magnetic stirring rod, so the solution quickly reacts with and effectively removes all the $CO_2$ while the unreactive nitrogen tracer rises into the outlet plenum 109 at the top of the chamber.

Preferably, for this process, the plenum 109 is initially loaded with a small volume, e.g. a few cubic centimeters, of a carrier gas in which the nitrogen-13 is soluble. This carrier may, for example, be nitrous oxide or other suitable biocompatible gas. It is also advantageous that the carrier be highly soluble in blood or aqueous solutions, so that as discussed further below, problems of bubble formation or potential danger of bends are avoided. Thus, operation of the receiving chamber 1 is such that the sweep gas or target predecessor material from the source is removed, and the cleansed or concentrated radionuclide resides in the plenum 109 with a carrier gas for transfer through the transfer valve to the flow path 21. The architecture of vessel 1 therefore retains the pocket of gas at the top of the chamber intact. In this way, no liquid infiltrates the tubing leading to the rest of the apparatus, where small droplets of liquid might cause false triggering of the liquid detector or blocking of the hydrophobic filter.

An important aspect of the design of the compliant compartment is that it is only compliant to positive volumes. That is, volume can be added to the chamber, but not withdrawn. Once the carbon dioxide is absorbed, and the bubble of nitrogen withdrawn, the membrane wall lies flat against the side wall of the chamber, and the chamber becomes rigid. Thus it is impossible to suck significant volumes of sodium hydroxide out of the absorbing chamber and into the rest of the system.

Figure 5A:
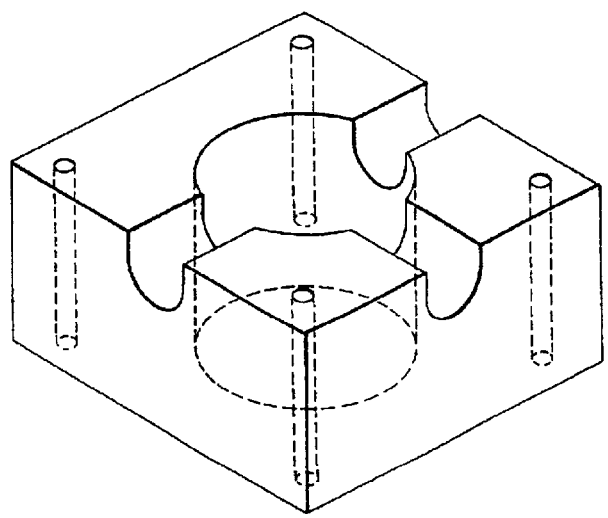
FIGS. 5A–5C illustrate stopcock mounting and control blocks of the console for use with a closed sterile set.
Figure 5:
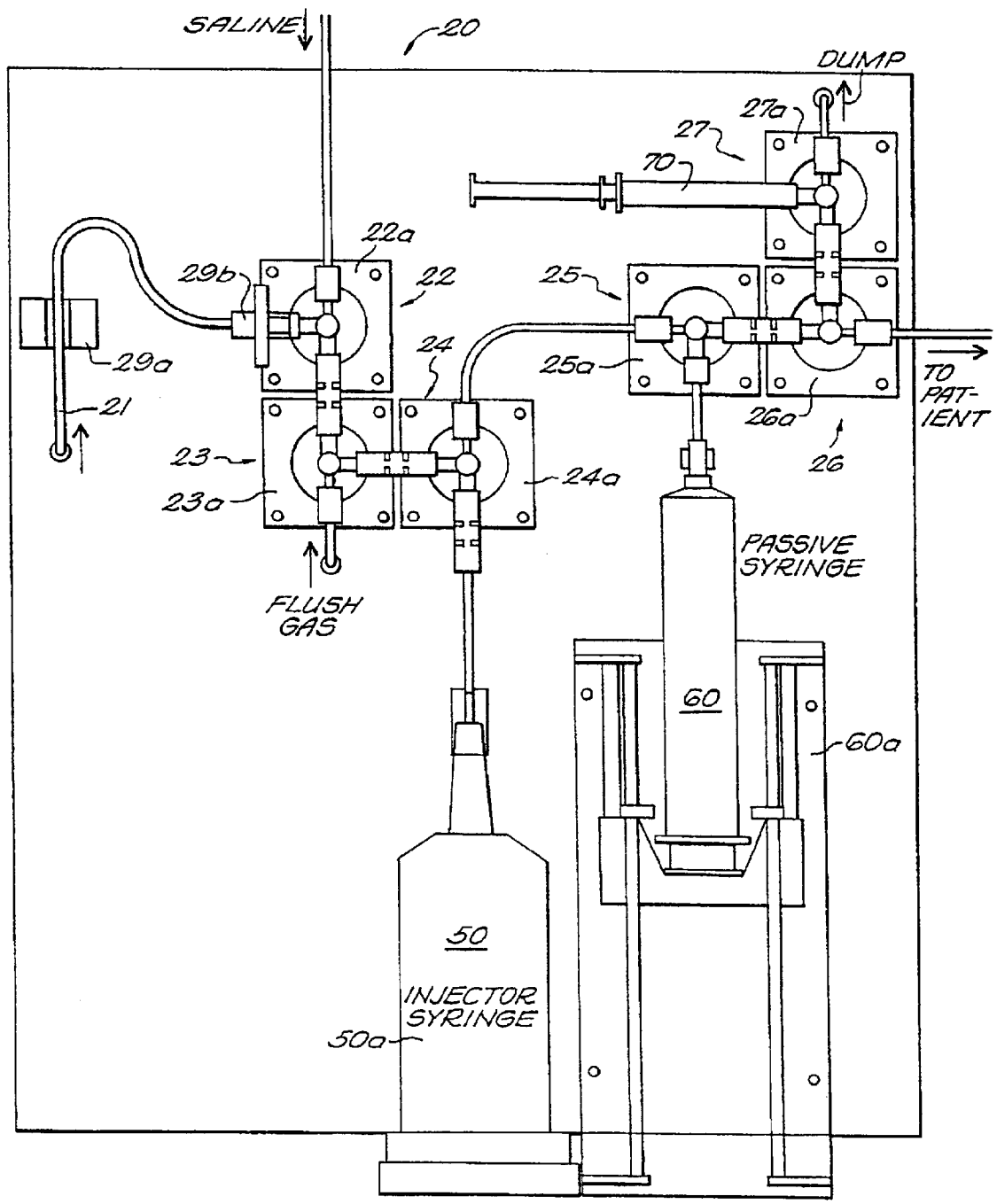
FIG. 5 illustrates an operating console for the set of the invention.

Skipping ahead to FIG. 5, there is shown a representative front panel of the console assembly 20 with the radionuclide entry port and elements of the flow path 21 laid out thereon. As shown, the flow line 21 first passes through a liquid detector which detects the arrival of liquid in the flow line from the chamber 1 and provides a control signal used, as described further below, for switching the states of the various stopcocks and transporting the bubble of radionuclide through the processing stages of the preparation assembly 10.

As further shown in FIG. 5 a hydrophobic filter 29b is placed in the flow line 21 as a barrier to entry of liquid from chamber 1 into the system 10. As shown, the fluid preparation line 21 or set, is positioned in the console 20 such that each of the stopcocks 22–27 fits within a corresponding receiving block 22a through 27a, and the injection syringe 50 and passive syringe 60 fit within a driver mounting 50a and a syringe support 60a, respectively. By way of example, the driver assembly for the injector syringe may be that of, or similar to, a manual or programmed contrast agent injector system capable of operation to drive a standard disposable syringe at high pressures through one or more precisely timed and controlled displacements to inject preset doses or volumes into the vascular system of a patient. The mounting 60a for the passive syringe may include a spring-loaded or counter-weighted platform or pushing member against which the distal end of the plunger of the injection syringe rides, so that the biased member returns the piston to its upper position (as shown) when the state of the stopcocks allows flow and the pressure in line 21 drops below the spring bias threshold.

Figure 5B:
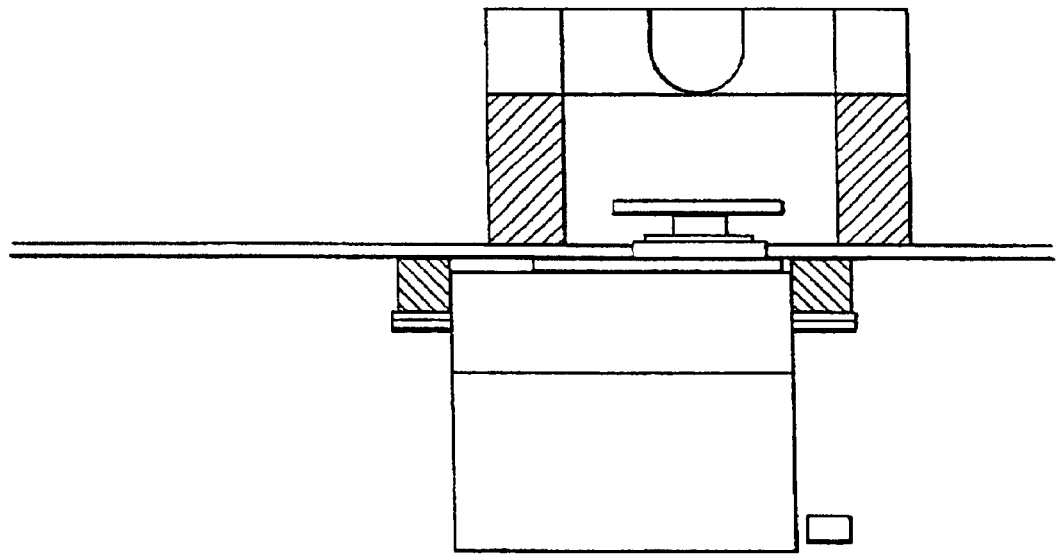
Figure 5C:
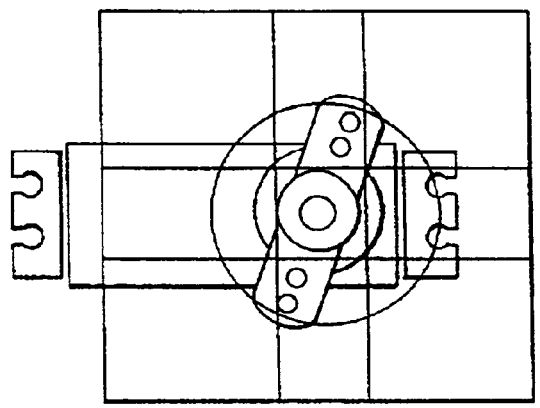

In the prototype embodiment, the injector drive consisted of a MedRad radiographic contrast injection instrument, and the remainder of the cabinet and control mechanism of unit 20 was built atop the injector mount so that the active syringe was conveniently located in immediate proximity to the other elements shown in FIG. 2. The stopcock mounting assemblies were prepared as shown in FIGS. 5A through 5C, by constructing shaped plastic receiving blocks having recesses each shaped to accept a standard disposable stopcock assembly therein and to mount on a plate so that each stopcock engages a position reporting actuator mechanism, which turns the handle of the stopcock. The stopcock was placed into the housing with the handle facing forward and the housing was designed to grip the three fluid connecting stubs of the stopcock, thus securely holding the stopcock body in a fixed position that allowed stopcock position to be controlled to within about one degree. A molded coupling was used to connect the stopcock handle to a standard servomotor, which in turn was controlled by a microcontroller board connected via a serial line to a computer used to control the apparatus. The computer was programmed to control operation of the stopcocks to define different segments for receiving, transferring, mixing and delivering the material. It was also programmed to control the injection regimen of the syringe for delivery of prepared doses to the patient.

In the prototype embodiment, the servomotor assemblies were modified so that the output of an internal potentiometer was passed to an A/D converter on the microcontroller board, and this output was used to calibrate the stopcock positions and then continuously monitor the position of each stopcock. Control software in the microprocessor with a graphical user interface allowed the user to set the position of the stopcock and displayed the position on the screen, signaling an alarm if a motor fails to drive a stopcock element to the programmed position. For preparing the nitrogen-13 tracer, the program was written to effect a sequence of control steps as described below, and delivery steps were controlled by using the injector both to control the preparation of the solution and the injection into the patient.

FIG. 4 illustrates a particular sequence for transfer of the tracer bubble from the absorbing chamber 1 into the mixing syringe, which is performed by encapsulating the tracer bubble with a saline solution. In broad terms, the operating sequence proceeded as follows. Before gas is received from the cyclotron the system is readied for production.

The tubing from the absorbing chamber is flushed with a gas and the remainder of the apparatus is flushed and filled with de-gassed saline solution. One suitable flush gas is nitrous oxide but many other gases may be used. The chief requirements are that the gas be biologically safe, soluble in water and be non-reactive with the reagents used (sodium hydroxide, in this case). The radioactive gas is then admitted to the absorbing chamber and is stirred with a magnetic stirrer until all carbon dioxide is absorbed. Stirring is performed gently to avoid generation of droplets which might clog the hydrophobic filter 29b (FIG. 5). The bubble of remaining gas at the top of the absorbing chamber is then transferred to the injector syringe which is otherwise filled with an appropriate amount of de-gassed saline for the contemplated infusion regiment or for the amount or available radionuclide. The mixture in the injector is next dissolved by repeatedly ejecting it into the passive syringe allowing its return and again ejecting it, so that by the vigorous flow and atomizing action of ejection the tracer is quickly dissolved in the saline solution. This process of vigorous atomization mixing by repeated passage through a flow segment between syringes in a closed set thus effectively addresses the difficult problem of preparing the radionuclide solution in a manner that is both safe and quick.

Next, with the stopcocks reset to define a different flow segment, a sample of the injectate so prepared is expelled from the syringe into the sampling syringe 80. Preferably a pH sensor is also present in the apparatus downstream of the injector syringe to detect any sodium hydroxide contamination which may have occurred, and to actuate a shutdown in that event. The strength of the prepared solution is determined and this data is entered in suitable program for the injection control or image processing. The stopcock configurations are again changed, and the injector then gives a rapid bolus of tracer solution along its output line into the patient.

Figure 4A:
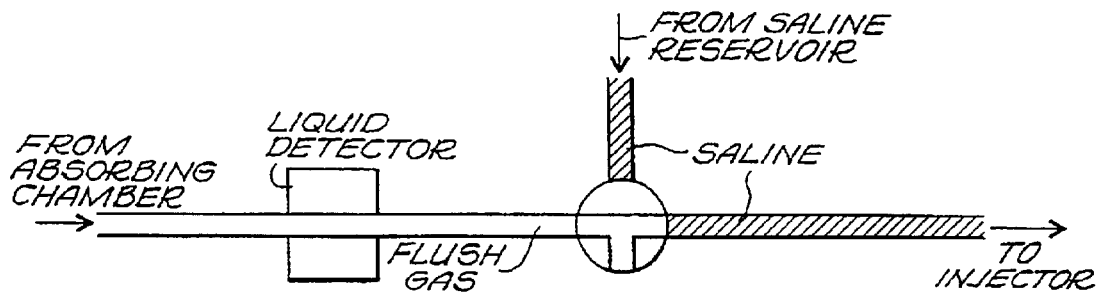
FIGS. 4A through 4D illustrate details of valve operation and flow for transfer of the radionuclide into a fluid handling set of the present invention.
Figure 4B:
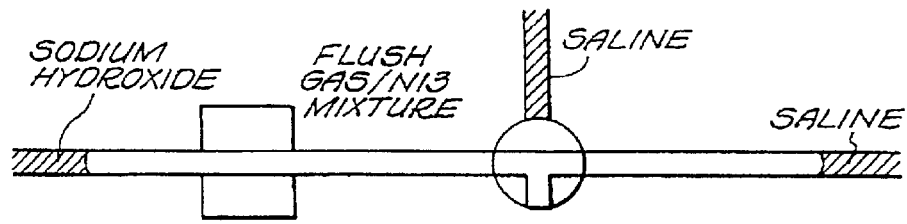
Figure 4C:
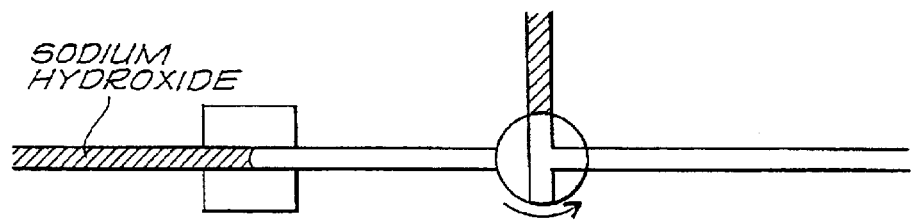
Figure 4D:
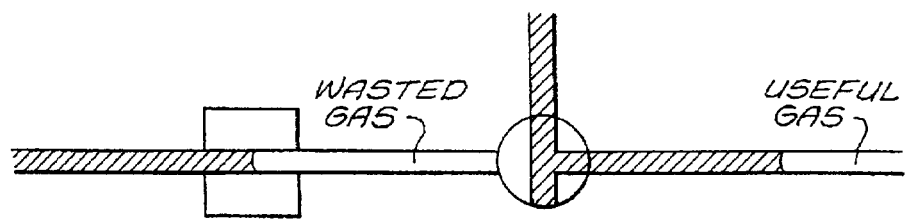

Returning now to FIG. 4, there is shown a representative sequence of states of the finite state flow segment operating sequence of the device, illustrating in this case the initial radionuclide transfer from the receiving chamber 1 into the preparation set 10. After the initial system preparation and cleansing in chamber 1 are completed, the state of the apparatus is as depicted in FIG. 4A. The upstream tubing (on the left) of stopcock 22 is filled with flush gas and the downstream tubing (to the right) is filled with degassed saline. The syringe 50 is then operated to draw along line 21 so that, as shown in FIG. 4B the bubble of radioactive gas is drawn out of the pocket 109 (FIG. 3), and toward the injector syringe 50. Sodium hydroxide solution is also drawn out of the absorbing chamber 1 at the trailing edge of the bubble of carrier/tracer gas. A liquid detector 29a is installed in the assembly 10 about the line 21 just upstream of the first stopcock 22 to provide a signal when the sodium hydroxide reaches this point. The transfer valve (FIG. 3) is then closed, and the controller moves the first stopcock (FIG. 4C) to connect the saline reservoir and fill in behind the bubble with saline solution from the reservoir. The bubble of tracer is thus "encapsulated" by saline solution as shown in FIG. 4D. This allows controlled transfer through the apparatus by operation of the injector syringe. A slight amount of tracer gas still residing in the first stopcock and liquid detector is wasted. However, it will be understood that all tubing interconnecting the various components in the processing section 10 is of small size (under one millimeter), of the type customarily used for transfer of small volumes of fluid, and thus the wasted tracer represents a very small proportion of the carrier/tracer bubble being processed.

After the bubble of gas is completely drawn into the injector syringe, the stopcocks are moved to define a new flow/transfer segment such that the injector outlet communicates only with the adjacent passive syringe. The mixture is then vigorously expelled into the passive syringe, then again drawn back into the active syringe and re-expelled. This process of repeated ejection promotes dissolution of the gas in several ways. Firstly, the surface area of the interface is increased exponentially by atomizing the fluid and in subsequent ejections breaking bubbles of gas into many smaller bubbles. Secondly, the ejection occurs at elevated pressure, thus enhancing the mechanisms of diffusion. Finally, the strong current and highly turbulent flow during ejection mixes the liquid very well, reducing any concentration gradients that might otherwise limit the process.

After the mixing process is complete, the stopcocks are again repositioned and the syringe 50 is operated to expel to the dump a volume equal to the volume of gas originally drawn into the syringe. This assures that any undissolved gas is ejected from the system. The lines to the patient are then flushed with the prepared tracer solution, and a small (1 ml) sample is taken. For the illustrated system, the sample is used primarily to assess the activity of the solution, but it could be additionally analyzed to check the composition of the injectate, or when applied to other radionuclide systems could determine other relevant conditions or parameters.

The pH of the solution is preferably measured by a sensor installed on the line to the dump tank. Any sodium hydroxide contamination is detected at this point, before injection to a patient.

In the foregoing system, it is important that the solution injected into the patient not be super-saturated and not contain any gas bubbles. If the solution were super-saturated, there would be a risk that bubbles could spontaneously appear in the solution before infusion or that microbubbles of nitrogen would form in the bloodstream causing an artificially-induced form of decompression sickness ('the bends'). To assure that supersaturation does not occur, the volume of nitrogen withdrawn from the absorbing chamber is limited to that volume which is known to dissolve in the volume of saline being prepared, and following dissolution, the mixture is allowed to equilibrate at atmospheric pressure. Thus, even if the solution is super-saturated, excess gas will diffuse out of the solution. Further, when, following the mixing described above, the volume at least as great as the volume of gas originally drawn in from the absorbing chamber is ejected from the top of the injector syringe to dump, both the excess undissolved gas and the gas that has come out of solution are expelled.

Preferably, an ultrasonic bubble detector is also installed on the line to the patient, as well as a bubble-trap filter. Prior to injection, the lines are flushed, and a final, visual check for microbubbles is performed.

Figure 6:
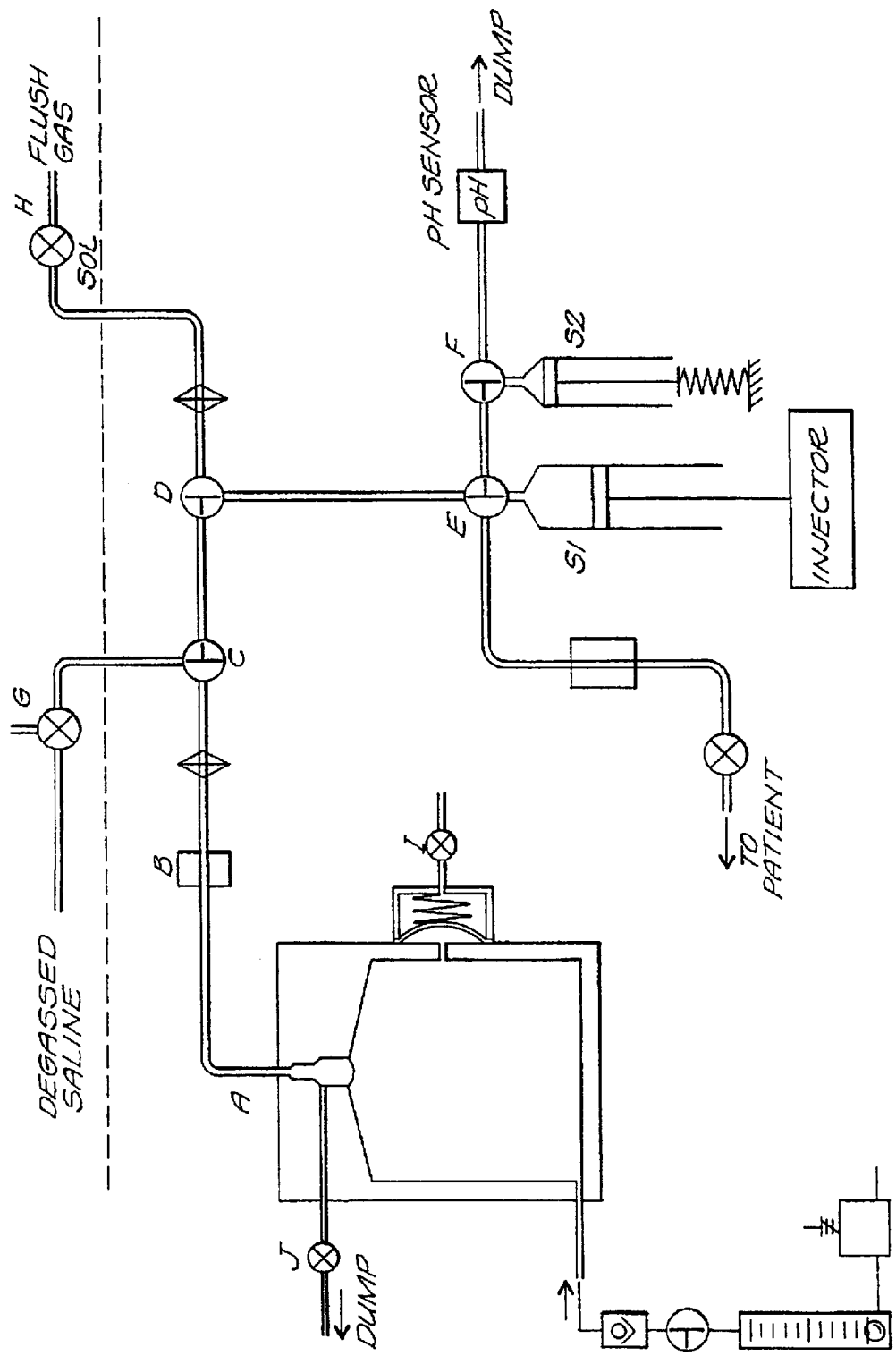
FIG. 6 illustrates another embodiment of the system and set.

FIG. 6 illustrates another embodiment of the system and set of the present invention. In this embodiment, the compliance chamber or flexible-walled side chamber may be actively pressed. This may be done to assure complete return of the flexible wall, and thus further guard against expulsion of the sodium hydroxide solution. Furthermore, the stopcocks are located somewhat differently to provide a short direct infusion path to the patient, and to separate or shift other paths or path segments. As in the first embodiment, the pressure syringe is centrally located, and serves as a hub for drawing, expelling or moving fluid along the various segment defined by the states of the stopcock valves. Advantageously, the pressure syringe mounts vertically, so that it initially receives and segregates the gas, and subsequently expels residual bubbles to the dump.

For operation of the system, the saline may be drawn from a USP-standard infusion bag, and all parts of the apparatus that contact the solution are assembled using aseptic technique from sterile, disposable medical components. Microporous filters are installed on the line entering the system from the saline bag, and on the line out of the system to the patient. Preferably a batch of tracer solution is prepared before the batch intended for infusion, and a sample is assayed.

Preferably, the bolus infusion of tracer is given by the injector under computer control, with the computer programmed to accurately control the infusate volume and rate, to effectively synchronize with a PET camera, and to automatically adjust dosage as the tracer decays. However, preferably the hardware is designed so that if necessary, the injector can be disconnected and operated manually. In the prototype embodiment using an existing, manually-operated contrast media injector, the addition of a microprocessor-based controller and other modifications made to the injector were such that all of its safety-features function normally, and when manually-operated, the injector was fundamentally the same device as an unmodified, FDA-approved original. The series architecture of the treatment vessel and mixing assembly, together with the unique bubble transfer mechanism and multiple redundant stops and operation safety checks thus forms a system that is safely interposed between a cyclotron target and the patient's vasculature. Repetitive ejection between syringes produces a highly effective mixing/solution mechanism using fungible disposables. Moreover, the provision of a closed, disposable set for handling and compounding the radionuclide in an automated negative pressure safety cabinet allows the operator to maintain a safe distance from radiation, and provides a convenient system for the remote handling and preparation of diverse medicines, reagents and tracer materials.

The invention has been described above in a particular application for receiving, preparing and injecting a gaseous radionuclide for pulmonary PET imaging. However, the unique remote handling, sterile mixing, and volumetric control achieved by the set and the operating console are applicable with slight changes to compounding and delivering medications, marking and synthesizing materials and other radiation-handling tasks. Thus, it should be understood that the invention is not to be limited by the particular embodiments shown and discussed above, but may take other forms and be embodied in diverse systems for preparing, reacting, formulating or delivering radionuclides or biologically active materials. The invention and its principals of operation being thus disclosed, one skilled in the art will appreciate further features and advantages of the invention, and will be lead to further variations and modifications of the invention. Accordingly, all such variations and modifications are considered to be within the spirit and scope of applicant's invention as defined by claims appended hereto and equivalents thereof. All publications and references cited herein are expressly incorporated herein by reference in their entirety.

What is claimed is:

1. A system for preparation and delivery of a biologically active, hazardous or radioactive fluid, the system comprising
a receiving system having a first port for receiving said fluid and a second port positioned for delivering said fluid
a fluid handling set including a syringe and a plurality of flushable valves interconnected as a closed unit by tubing extending to an outlet
the syringe connecting via said fluid handling set to said second port and to said outlet for drawing the fluid into the tubing and transferring said fluid to the outlet as a prepared liquid
and the fluid handling set being configured for operation of said valves to define a finite set of flow segments at different times in said set such that the syringe flushes, fills prepares and delivers the prepared fluid without exposing the operator to radiation.

2. A system for preparation and delivery of a biologically active, hazardous or radioactive material such as a gas, the system comprising a receiving chamber having a first port for receiving said fluid and a second port positioned for accessing an active gas present in said material an operating assembly for mounting a fluid handling set including a pressure syringe, a passive syringe and a plurality of flushable valves interconnected as a closed unit by tubing such that tie tubing connects to said second port, and the operating assembly being configured to secure and operate the pressure syringe and the plurality of valves in sequence such that the pressure syringe draws the material into the pressure syringe and transfers the material with liquid to said passive syringe so as to form a prepared liquid, and further operating said valves to define a finite set of flow segments at different times in said set for flushing, filling, preparing and delivering the prepared liquid, to receive the material from a source and provide the prepared liquid to a patient.

3. A system for preparation and delivery of a biologically active, hazardous or radioactive material, the system comprising a receiving chamber having a first port for receiving said material and a second port positioned for accumulating a desired portion of the material a fluid handling set including a plurality of flushable valves interconnected as a closed unit by tubing and configured for automated remote operation of said valves to form a finite state flow path effective to receive and encapsulate said desired portion as a bubble, prepare said portion in a delivery liquid and transfer the delivery liquid to an output.

4. The system of claim 3, wherein said valves define flow segments at different times in said set for flushing, filling, preparing and delivering the material such that the set receives the material as a gas from a source and safely delivers the delivery liquid to the bloodstream of a patient.

5. The system of claim 4, wherein the fluid handling set includes a pressure syringe operable for drawing the material into the set, mixing the delivery liquid, and delivering the delivery liquid into the bloodstream of a patient.

6. The system of claim 3, wherein the system prepares a gaseous radionuclide for injection to perform positron emission tomographic images of the patient.

7. The system of claim 3, wherein the fluid handling set is sterile assembly and further comprises and active syringe connected to one of said valves, and a passive syringe connected to another of said valves for receiving liquid such that the set is operable to prepare said portion in said delivery liquid by ejecting said portion and delivery liquid from the active syringe into the passive syringe.

8. A system for sterile preparation of a fluid radionuclide for use, such system comprising a sterile flow set including an inlet, an outlet, a plurality of stopcocks arranged in a sequence along a flow line to define a plurality of fluid transport segments, and first and second syringes connected to the flow line being operable to form a sterile liquid solution of said radionuclide while it remains in the flow set by repeated ejection from said first syringe to said second syringe and return to said first syringe.

9. A system according to claim 8, wherein the sterile flow set includes at least five stopcocks.

10. A system according to claim 8, wherein at least one of said syringes attaches directly to a port of one of the stopcocks.

11. A fluid handling set for use in receiving a hazardous fluid material and forming a delivery liquid, such set comprising a plurality of at least five stopcocks and tubing Interconnecting said plurality of stopcocks to form a closed transport path for handling the hazardous fluid material, each stopcock further having a port for admitting material to or expelling material from said closed transport path.

12. A device for receiving a hazardous fluid material and forming a delivery liquid such as a reagent, medicine or imaging agent containing said fluid material, such device comprising a plurality of stopcock receptacles arranged along a path, a corresponding plurality of servomotors positioned and configured for individually controlling a stopcock each being positioned in one of the receptacles, a syringe driver, and a controller operative to control said servomotors to form a set of flow segments along a closed transport path for handling the hazardous fluid material, and to control said syringe driver to drive a syringe so that the syringe draws said fluid material into the transport path and moves the fluid material along ones of said flow segments so as to prepare and deliver the delivery fluid.

13. The device of claim 12, further comprising a flow set including a plurality of stopcocks interconnected by tubing to form a sterile flow path, an active syringe connected to said flow path, and a passive syringe connected to said flow path.

14. The device of claim 13, wherein the controller is operative to control said servomotors to define a path between the active syringe and the passive syringe, and to prepare the fluid material by repeated ejection of the material from the active syringe to the passive syringe.

* * * * *